United States Patent
Molaire

(10) Patent No.: US 7,008,742 B2
(45) Date of Patent: Mar. 7, 2006

(54) HEAT-INDUCED FORMATION OF CO-CRYSTALLINE COMPOSITION CONTAINING TITANYL PHTHALOCYANINE AND TITANYL FLUOROPHTHALOCYANINE

(75) Inventor: Michel F. Molaire, Rochester, NY (US)

(73) Assignee: Eastman Kodak Company, Rochester, NY (US)

(*) Notice: Subject to any disclaimer, the term of this patent is extended or adjusted under 35 U.S.C. 154(b) by 0 days.

(21) Appl. No.: 11/021,082

(22) Filed: Dec. 21, 2004

(65) Prior Publication Data

US 2005/0159595 A1 Jul. 21, 2005

Related U.S. Application Data

(60) Provisional application No. 60/532,441, filed on Dec. 24, 2003.

(51) Int. Cl.
*G03G 15/02* (2006.01)
*A61B 5/055* (2006.01)
*A61B 10/00* (2006.01)
*C07B 47/00* (2006.01)
*C07F 5/10* (2006.01)

(52) U.S. Cl. .................. 430/59.5; 430/59.4; 424/9.362; 424/9.61; 534/15; 540/145; 514/185; 514/410

(58) Field of Classification Search ............. 424/9.362, 424/9.61; 540/145; 534/15; 514/185, 410; 430/59.5
See application file for complete search history.

(56) References Cited

U.S. PATENT DOCUMENTS

| 4,701,396 | A | 10/1987 | Hung et al. |
| 5,166,339 | A | 11/1992 | Duff et al. |
| 5,238,764 | A | 8/1993 | Molaire et al. |
| 5,523,189 | A | 6/1996 | Molaire |
| 5,614,342 | A | 3/1997 | Molaire et al. |
| 5,629,418 | A | 5/1997 | Molaire et al. |
| 5,766,810 | A | 6/1998 | Molaire et al. |
| 5,773,181 | A | 6/1998 | Molaire et al. |
| 2004/0106053 | A1 * | 6/2004 | Molaire et al. ............ 430/59.5 |

OTHER PUBLICATIONS

Paul Borsenberger, et al., "Organic Photoreceptors for Imaging Systems", pp. 339-391.

* cited by examiner

*Primary Examiner*—James O. Wilson
*Assistant Examiner*—Matthew L. Fedowitz
(74) *Attorney, Agent, or Firm*—Carl F Ruoff

(57) ABSTRACT

A process for forming a cocrystalline mixture of titanyl phthalocyanine (TiOPc) and titanyl fluorophthalocyanine (TiOFPc) includes: dry milling a mixture of crude TiOPc and crude TiOFPc, thereby forming an amorphous pigment mixture of TiOPc and TiOFPc; and heating the amorphous pigment mixture at a temperature effective to form a cocrystalline composition comprising titanyl phthalocyanine (TiOPc) and titanyl fluorophthalocyanine (TiOFPc), the cocrystalline composition being characterized by an X-ray diffraction spectrum exhibiting intensity peaks at 7.2°, 12.9°, 16.3°, 22.3°, 24.6°, 26.2°, and 28.8° with respect to X-rays of Cu Kα at a wavelength of 1.54 1 Å of the Bragg angle 2θ.

7 Claims, 6 Drawing Sheets

HEAT-INDUCED FORMATION OF CO-CRYSTALLINE COMPOSITION CONTAINING TITANYL PHTHALOCYANINE AND TITANYL FLUOROPHTHALOCYANINE

CROSS-REFERENCE TO RELATED APPLICATIONS

This application claims the benefit of U.S. Provisional Patent Application Ser. No. 60/532,441 filed Dec. 24, 2003.

Reference is made to the following co-pending, commonly-assigned applications, the disclosures of which are incorporated herein by reference:

U.S. patent application Ser. No. 10/655,528, filed on Sep. 4, 2003, by Molaire et al., entitled: SELF-DISPERSING TITANYL PHTHALOCYANINE PIGMENT COMPOSITIONS AND ELECTROPHOTOGRAPHIC CHARGE GENERATION LAYERS CONTAINING SAME;

U.S. patent application Ser. No. 10/653,573, filed on Sep. 2, 2003, by Molaire, entitled: UNIFORM COCRYSTALS OF TITANYL FLUOROPHTHALOCYANINE AND TITANYL PHTHALOCYANINE FORMED IN TRICHLOROETHANE, AND CHARGE GENERATING LAYER CONTAINING SAME;

U.S. patent application Ser. No. 10/655,113, filed on Sep. 4, 2003, by Molaire et al., entitled: COCRYSTALS CONTAINING HIGH-CHLORINE TITANYL PHTHALOCYANINE AND LOW CONCENTRATION OF TITANYL FLUOROPHTHALOCYANINE, AND ELECTROPHOTOGRAPHIC ELEMENT CONTAINING SAME;

U.S. patent application Ser. No. 10/655,388, filed on Sep. 4, 2003, by Molaire et al., entitled: TWO-STAGE MILLING PROCESS FOR PREPARING COCRYSTALS OF TITANYL FLUOROPHTHALOCYANINE AND TITANYL PHTHALOCYANINE, AND ELECTROPHOTOGRAPHIC ELEMENT CONTAINING SAME; and U.S. patent application Ser. No. 10/655,289, filed on Sep. 4, 2003, by Molaire et al., entitled: PROCESS FOR FORMING COCRYSTALS CONTAINING CHLORINE-FREE TITANYL PHTHALOCYANINES AND LOW CONCENTRATION OF TITANYL FLUOROPHTHALOCYANINE USING ORGANIC MILLING AID.

FIELD OF THE INVENTION

The present invention relates to electrophotographic elements and related materials. More particularly, the invention relates to a process for forming a cocrystalline composition containing titanyl phthalocyanine (TiOPc) and titanyl tetrafluorophthalocyanine (TiOFPc) by heating an amorphous mixture of TiOPc and TiOFPc.

BACKGROUND OF THE INVENTION

In electrophotography, an image comprising a pattern of electrostatic potential, also referred to as an electrostatic latent image, is formed on a surface of an electrophotographic element comprising at least two layers: a photoconductive layer and an electrically conductive substrate. The electrostatic latent image can be formed by a variety of mechanisms, for example, by image-wise radiation-induced discharge of a uniform potential previously formed on the surface. Typically, the electrostatic latent image is then developed into a toner image by contacting the latent image with an electrographic developer. If desired, the latent image can be transferred to another surface before development.

Among the many different kinds of photoconductive materials that have been employed in electrophotographic elements are phthalocyanine pigments such as titanyl phthalocyanine and titanyl tetrafluorophthalocyanines. Electrophotographic recording elements, containing such pigments as charge-generation materials, are useful in electrophotographic laser beam printers because of their capability for providing good photosensitivity in the near infrared region of the electromagnetic spectrum, that is, in the range of 700–900 nm.

In a photoconductive layer produced from a liquid coating composition that includes the titanyl phthalocyanine pigment and a solvent solution of polymeric binder, it is necessary that the titanyl phthalocyanine pigment be in a highly photoconductive form, either crystalline or amorphous, and in a sufficiently stable dispersion to permit its application as a very thin layer having high electrophotographic speed in the near infrared region.

A variety of methods have been used to produce suitable forms of titanyl phthalocyanine having differing crystallographic characteristics. U.S. Pat. No. 5,166,339 includes a table of polymorphs of unsubstituted titanyl phthalocyanine in which materials bearing multiple designations are grouped as four types. Many phthalocyanine pigments are discussed in P. M. Borsenberger and D. S. Weiss, *Organic Photoreceptors for Imaging Systems*, Marcel Dekker, Inc., New York, pp. 338–391.

In one type of preparation, commonly referred to as "acid-pasting", crude titanyl phthalocyanine is dissolved in an acid solution, which is then diluted with a non-solvent to precipitate the titanyl phthalocyanine product. In another type of procedure, the crude titanyl phthalocyanine is milled, generally with particular milling media. Additionally, some preparations include a combination of techniques or modify a previously prepared titanyl phthalocyanine.

U.S. Pat. Nos. 5,238,764 and 5,238,766, the disclosures of which are incorporated herein by reference, teach that titanyl fluorophthalocyanine products of acid-pasting and salt-milling procedures, unlike unsubstituted titanyl phthalocyanine, suffer a significant reduction in near infrared sensitivity when they are dispersed in a solvent such as methanol or tetrahydrofuran, which has a $gamma_c$ hydrogen bonding parameter value greater than 9.0. These patents further teach that this reduction in sensitivity can be prevented by first contacting the titanyl fluorophthalocyanine with a material having a $gamma_c$ hydrogen bonding parameter of less than 8.0.

U.S. Pat. No. 5,629,418, the disclosure of which is incorporated herein by reference, describes a method for preparing titanyl fluorophthalocyanine that provides the steps of: dissolving titanyl fluorophthalocyanine in acid to form a solution; admixing the solution and water to precipitate out amorphous titanyl fluorophthalocyanine; washing the amorphous titanyl fluorophthalocyanine until substantially all of the acid is removed and contacting it with an organic solvent, which results in the conversion of the amorphous material to high crystallinity titanyl fluorophthalocyanine, the amorphous titanyl fluorophthalocyanine having been maintained in contact with water continuously from its precipitation to its conversion to a crystalline form.

U.S. Pat. No. 5,523,189, the disclosure of which is incorporated herein by reference, describes an electrophotographic element including a charge generation layer that includes a binder in which is dispersed a physical mixture of a high speed titanyl fluorophthalocyanine having a first intensity peak with respect to X-rays characteristic of Cu Kα at a wavelength of 1.541 Å of the Bragg angle 2θ at 27°±0.2°, and a second intensity peak at 7.3°±0.2°, the second peak having an intensity relative to the first peak of less than 60 percent; and a low speed titanyl fluorophthalocyanine having a first intensity peak with respect to X-rays characteristic of Cu Kα at a wavelength of 1.541 Å of the Bragg angle 2θ at 6.7°±0.2°, and a second intensity peak at 23°±0.2°, the second peak having an intensity relative to the first peak of less than 50 percent.

U.S. Pat. No. 5,773,181, the disclosure of which is incorporated herein by reference, describes a method for preparing a phthalocyanine composition providing the steps of: synthesizing a crystalline product comprising a mixture of five different unsubstituted or fluorosubstituted phthalocyanines, wherein a central M moiety bonded to the four inner nitrogen atoms of the phthalocyanine nuclei represents a pair of hydrogen atoms or a covalent or coordinate bonded moiety, including an atom selected from the group consisting of: Li, Na, K, Be, Mg, Ca, Ba, Sc, Y, La, Ac, Ti, Zr, Hf, V, Nb, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, and Sb, with M preferably representing Ti=O;

increasing the amorphous character of the mixture of phthalocyanines as determined by X-ray crystallography using X-radiation characteristic of Cu Kα at a wavelength of 1.541 Å of the Bragg angle 2θ to provide an amorphous pigment mixture;

contacting the amorphous pigment mixture with organic solvent having a gamma$_c$ hydrogen bonding parameter of less than 8.0; and prior to the contacting, substantially excluding the amorphous pigment mixture from contact with organic solvent having a gamma$_c$ hydrogen bonding parameter greater than 9.0.

The particle size distribution and stability of charge generation dispersions are very important for providing uniform charge generation layer in order to control generation of "breakdown spots" and minimize the granularity of prints. U.S. Pat. Nos. 5,614,342 and 5,766,810, the disclosures of which are incorporated herein by reference, describes a method for preparing cocrystals of titanyl fluorophthalocyanine and unsubstituted titanyl phthalocyanine that provides the steps of: admixing crude titanyl phthalocyanine and crude titanyl fluorophthalocyanine to provide an amorphous pigment mixture, as determined by X-ray crystallography using X-radiation characteristic of Cu Kα at a wavelength of 1.541 Å of the Bragg angle 2θ; contacting the amorphous pigment mixture with an organic solvent having a gamma$_c$ hydrogen bonding parameter of less than 8:0; and, prior to contacting, substantially excluding the amorphous pigment mixture from contact with an organic solvent having a gamma$_c$ hydrogen bonding parameter greater than 9.0. The amorphization step must be substantially complete so as to break the large primary particles of the starting crude pigments and thereby lower the average particle size of the final cocrystalline mixture. Substantially complete amorphization of the crude pigments is also necessary to prevent degradation of the dark decay characteristics of the final cocrystal; small amounts of crude pigments having inherently high dark decay that are not amorphized would not be affected by the subsequent solvent treatment and therefore would retain their high dark decay characteristics, causing degradation of the dark decay property of the final cocrystalline product.

The final step in the method of U.S. Pat. No. 5,614,342 entails contacting the cocrystalline pigment with an organic solvent having a gamma$_c$ hydrogen bonding parameter of less than 8:0, for example, a chlorinated solvent such as dichloromethane or 1,1,2 trichloroethane. After the organic solvent treatment, the pigment has to be filtered and dried, a procedure that is rather time consuming.

In the previously mentioned U.S. patent application Ser. No. 10/655,388, a method of isolating an amorphous mixture of titanyl phthalocyanine and fluorinated titanyl phthalocyanine is disclosed that involves the use of water as an isolation medium. It has now unexpectedly been found that the amorphous mixture made by this method can undergo heat-induced crystallization in the dry state to form a cocrystalline composition different from that obtained in the presence of organic solvents or water.

SUMMARY OF THE INVENTION

The present invention is directed to a process for forming a cocrystalline mixture of titanyl phthalocyanine (TiOPc) and titanyl fluorophthalocyanine (TiOFPc) by: dry milling a mixture of crude TiOPc and crude TiOFPc, thereby forming an amorphous pigment mixture of TiOPc and TiOFPc; and heating the amorphous pigment mixture at a temperature effective to form a cocrystalline composition comprising titanyl phthalocyanine (TiOPc) and titanyl fluorophthalocyanine (TiOFPc), the cocrystalline composition being characterized by an X-ray diffraction spectrum exhibiting intensity peaks at 7.2°, 12.9°, 16.3°, 22.3°, 24.6°, 26.2°, and 28.8° with respect to X-rays of Cu Kα at a wavelength of 1.54 1 Å of the Bragg angle 2θ.

BRIEF DESCRIPTION OF THE DRAWINGS

FIG. 1: an amorphized TiOPc/TiOFPc pigment;

FIG. 2: a cocrystalline TiOPc/TiOFPc mixture obtained by heating the amorphized pigment of FIG. 1;

FIG. 3: a cocrystalline TiOPc/TiOFPc mixture obtained by dichloromethane treatment of the amorphized pigment of FIG. 1;

FIG. 4: a cocrystalline TiOPc/TiOFPc mixture obtained by dichloromethane treatment of the cocrystalline TiOPc/TiOFPc mixture resulting from heating the amorphized pigment of FIG. 1;

FIG. 5: a mixture of crystalline TiOPc and crystalline TiOFPc resulting from methanol treatment of the amorphized pigment of FIG. 1; and FIG. 6: the cocrystalline TiOPc/TiOFPc mixture of FIG. 2 after treatment with methanol.

DETAILED DESCRIPTION OF THE INVENTION

Figure 1:
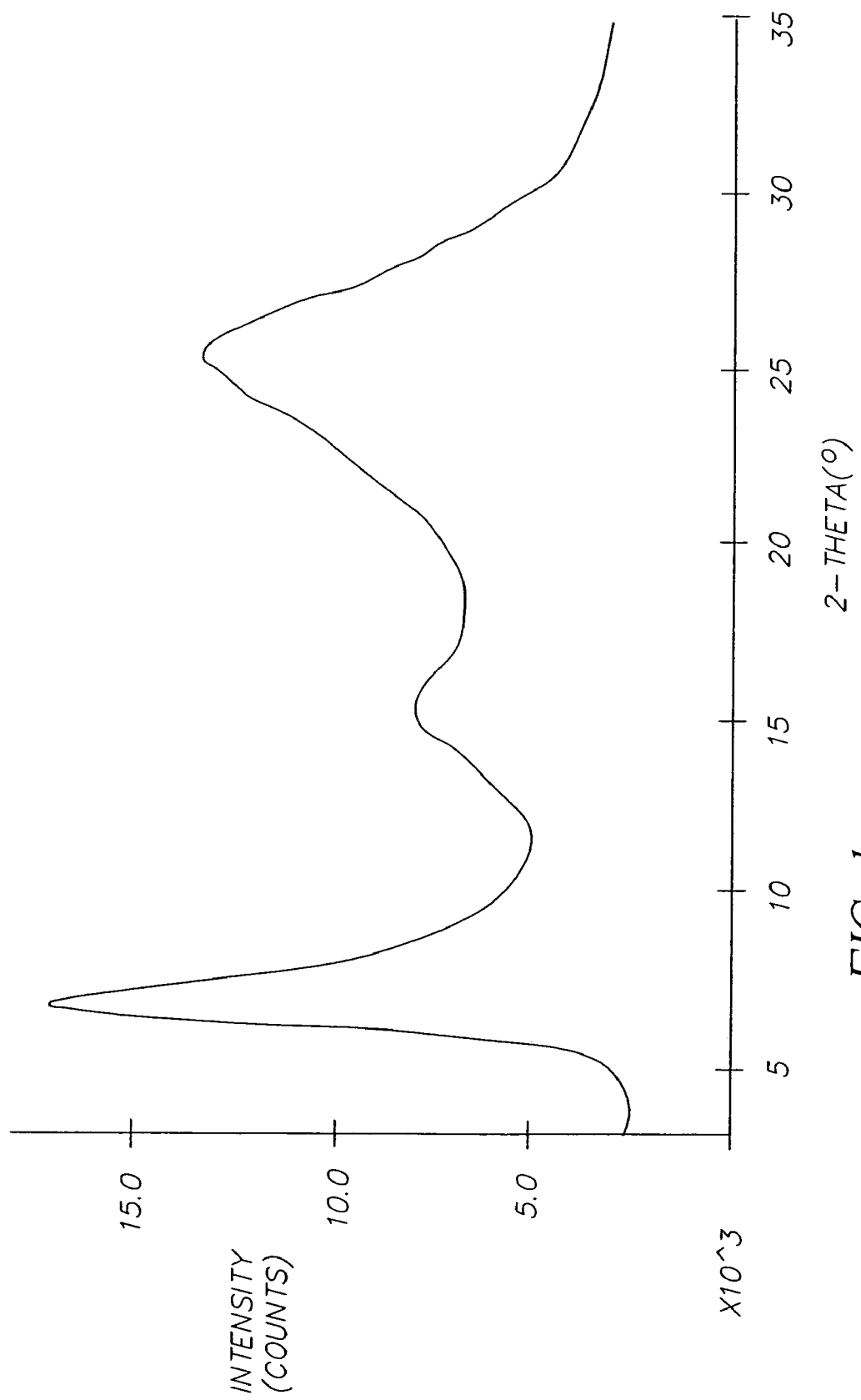
FIGS. 1–6 are X-ray diffraction spectra showing peaks of the Bragg angle 2θ with respect to X-rays of Cu Kα at a wavelength of 1.541 Å for mixtures of TiOPc and TiOFPc, as follows.

Unsubstituted titanyl phthalocyanine, abbreviated throughout this application as "TiOPc", has the following structural formula:

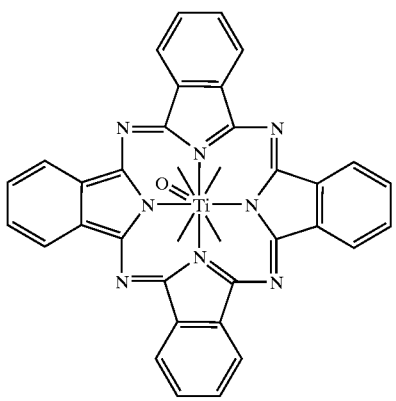

Titanyl fluorophthalocyanines, abbreviated herein as "TiFOPc", have the following structural formula: each of k, l, m and n is independently an integer from 1 to 4. In a particular embodiment of the invention, the crystalline titanyl fluorophthalocyanine is a mixture comprising titanyl 2,9,16,23-tetrafluorophthalocyanine, titanyl 2,9,16-trifluorophthalocyanine, titanyl 2-fluorophthalocyanine, titanyl 2,9-difluorophthalocyanine, and titanyl 2,16-difluorophthalocyanine.

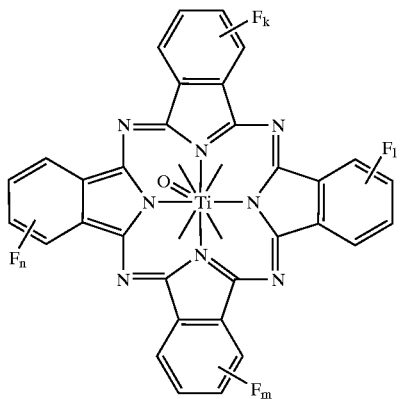

The composition of the mixture and their electrophotographic properties can be manipulated through varying the weight ratio of the fluorophthalocyanines. The characteristics of the phthalocyanines combined to form the crude mixture are determined by the desired photogeneration characteristics of the final product. The cocrystalline composition of the present invention contains TiOPc and TiOFPc in a TiOPc:TiOFPc weight ratio of, preferably about 90:10 to about 50:50, more preferably, about 75:25 to about 65:35.

In accordance with the process of the invention, crude titanyl phthalocyanine and titanyl fluorophthalocyanine are first admixed by dry milling to form an amorphous pigment mixture of TiOPc and TiOFPc. The crude materials can be synthesized by a number of well-known procedures, for example, those described in the previously discussed U.S. Pat. Nos. 4,701,396 and 5,614,342. As synthesized, titanyl phthalocyanine pigments normally have a particle size that is too large for them to be effectively used in electrophotographic applications. In this condition, they are known in the art as "crude" pigments. Such crude pigments normally have a particle size in excess of 10 micrometers, often a particle size of at least 50 micrometers, and in some cases, at least 1 millimeter. The term "particle size" is used herein to refer to the largest dimension of an individual particle and the median value of the same parameter for the particles of a particulate. Particle size can be readily determined from electron photomicrographs using techniques well known to those skilled in the art.

After admixing, the amorphous nature of the crude pigment mixture is established by X-ray crystallography. The crystallographic characteristics discussed herein, i.e., amorphousness and crystallinity, are based upon X-ray diffraction spectra at the Bragg angle $2\theta$ using Cu K$\alpha$ X-radiation at a wavelength of 1.541 Å and are ±0.2.degree, unless otherwise indicated. Suitable X-ray diffraction techniques are described, for example, in *Engineering Solids*, T. S. Hutchinson and D. C. Baird, John Wiley and Sons, Inc., 1963, and *X-ray Diffraction Procedures for Polycrvstalline and Amorphous Materials*, 2nd Ed., John Wiley and Sons, Inc., 1974.

In the preparation of the amorphous mixture by dry milling, the crude pigment mixture is mechanically ground in the dry state under shear conditions that break up particle agglomerates, reduce the particle size, and render the mixture less crystalline, i.e. more amorphous. It is preferred that dry milling be continued until the pigment mixture is rendered substantially or fully amorphous. The term "fully amorphous", as used herein, refers to a crystalline/amorphous state in which the well defined peaks of the crude phthalocyanine are replaced by a very high baseline response modulated by a few very broad, 5–10 degree or wider peaks.

The dry milling procedure is carried out in the substantial absence of any solvent, or polymeric binder, or salt. Milling apparatus capable of providing the necessary shear are well known and include, for example, conventional ball mills, roll mills, paint shakers, vibrating mills, and the apparatus described in U.S. Pat. Nos. 4,555,467 and 4,785,999. The shear employed is varied, as is well known to those skilled in the art, depending upon such factors as the type of milling apparatus, milling aids such as steel balls, and the crude pigment mixture used. The energy applied in the first milling stage generally does not exceed about 5 watts, and is typically from about 3 to 5 watts. Enough energy is applied to convert the crude pigment mixture to a low crystallinity pigment mixture.

The milling apparatus used during the dry milling stage may or may not require the use of particulate milling aids: materials added to the pigment particles to increase shear and decrease milling time. Particulate milling aids suitable for use in the claimed invention are materials that can be easily removed from the milled pigment mixture. For example, the salts described as milling aids in U.S. Pat. No. 5,055,368 are not desirable for use as particulate milling aids because the salts themselves are degraded to very small size by milling and must be removed by extensive washing. Examples of preferred particulate milling aids are steel shot, ceramic, glass, and zirconia media. These aids typically are available in sizes from about 0.5 to about 5 millimeters in diameter. Typically, the concentration of the pigment mixture during milling is from about 0.5 to 25 weight percent relative to the total weight of the pigment mixture and the milling media. The dry milling time will vary greatly depending upon a number of factors such as relative proportions of pigment mixture and milling aid and the specific milling equipment used. Generally, a suitable time for the dry milling stage may be as much as 240 hours, with typical times being in the range of from about 0.5 to 120 hours.

Milling tends to result in the liberation of heat, which would raise the temperature of the milled composition. It is desirable that the milling apparatus include temperature-regulating means to help maintain the temperature below the decomposition temperature of the phthalocyanine pigments, preferably in the range of about 0° C. to about 150° C., more preferably about 40° C. to about 100° C.

A suitable milling apparatus is the Sweco Vibro Energy grinding mill, manufactured by Sweco, Inc., Florence, Ky. Stainless steel beads, 2 mm in diameter, are added as a milling media on a 90 wt./wt. percent basis relative to the weight of the pigment mixture, which is milled for a time period of about 12 to about 96 hours at temperatures of about 25° C. to about 60° C.

The amorphous pigment mixture obtained by dry milling is preferably characterized by an X-ray diffraction spectrum exhibiting intensity peaks at 7.2°, 15.4°, and 25.5°, all at ±0.2°, with respect to X-rays of Cu Kα at a wavelength of 1.541 Å of the Bragg angle 2θ.

Preparation 1

Crude Substantially Chlorine-Free Titanyl Phthalocyanine (TiOPc)

Phthalonitrile (1280 g), benzamide (1512.5 g), xylene (1250 ml), and pentanol (1052 g) were added in that order into a 12-liter 3-necked round-bottomed flask equipped with a temperature probe and temperature controller, a condenser, and a paddle stirrer. After the stirrer was started, titanium (IV) butoxide (838 g), and xylene (1000 ml) were added. The reaction mixture was heated to reflux (144° C.) for six hours, then cooled to 85° C., and filtered through a medium frit sintered glass funnel. The pigment was rinsed first with 4×500-ml portions of toluene and then with 4×500-ml portions of hot dimethylformamide. After an overnight soak in dimethylformamide, the mixture was heated at reflux in that solvent for one hour. The product was collected and washed with methanol and acetone, then dried at 70–80° C. overnight. Neutron activation indicated 8.6±0.02 wt. % titanium and less than 0.01 wt. % chlorine.

Preparation 2

Crude Titanyl Tetrafluorophthalocyanine (TiOFPc)

Crude titanyl tetrafluorophthalocyanine was prepared as described in Preparation 2 of U.S. Pat. No. 5,614,342.

The crude TiOPc and TiOFPc pigments prepared as just described were employed in the following examples illustrating the invention.

EXAMPLE 1

Preparation of Amorphous TiOPc/TiOFPc 60:40 Mixture

A 1-gallon-wide mouth glass jar was filled with 9 kg of 3-mm diameter stainless steel balls, 45 g of crude TiOPc of Preparation 1, and 30 g of TiOFPc of Preparation 2, then put on a roller mill at 85 rpm. After milling of the mixture for 120 hours, 1.5 liters of water was added, and the mixture was milled for another 24 hours. After removal of the steel balls, the pigment was separated and dried at 110° C. for about 4 hours. A sample of the pigment was sent for x-ray crystallographic analysis for assessment of amorphicity. In the plot of intensity vs Bragg angle 2θ shown in FIG. 1, the three broad peaks are characteristic of an amorphized TiOPc/TiOFPc mixture.

EXAMPLE 2

Heat-Induced Crystallization of Amorphized TiOPc/TiOFPc Mixture

Three samples of the amorphized TiOPc/TiOFPc mixture obtained in Example 1 were submitted to differential scanning calorimetric (DSC) testing. All three samples exhibited an exotherm at about 196–200° C. (~13–14 J/gram), suggesting that the amorphized mixture had undergone heat-induced crystallization in the course of the DSC testing procedure.

In accordance with the present invention, the dry amorphous pigment mixture is heated at a temperature of, preferably, about 150° C. to about 250° C., more preferably, about 170° C. to about 220° C., to effect its conversion to the cocrystalline composition containing titanyl phthalocyanine (TiOPc) and titanyl fluorophthalocyanine (TiOFPc). Heating of the dry amorphous pigment mixture to convert it to the cocrystalline composition is carried out for a period of about 15 minutes to about 3 hours, more preferably, about 30 minutes to about 2 hours.

A sample of the amorphized pigment mixture from Example 1 was heat treated in a Blue M oven for 30 minutes at 210° C. X-ray diffraction analysis of the heat-treated material indicated conversion to a crystalline material characterized by the distinctive diffractogram depicted in FIG. 2, having intensity peaks at 7.2°, 12.9°, 16.3°, 22.3°, 24.6°, 26.2°, and 28.8° with respect to X-rays characteristic of Cu Kα at a wavelength of 1.541 Å of the Bragg angle 2θ.

Subjecting the crystalline material obtained by heat treatment to DSC test conditions produced no exotherm, which is indicative of the absence of amorphous material. The heat-treated crystalline pigment sample was further heated in the Blue M oven at 210° C. for another 2.5 hours and again subjected to X-ray analysis. The additional heating produced no change in the X-ray diffractogram shown in FIG. 2. Further heating for 2.5 hours at 225° C. still failed to cause any change in the diffractogram.

EXAMPLE 3

Solvent Treatment of TiOPc/TiOFPc Mixture a) A sample of the amorphized mixture of Example 1 was treated in dichloromethane for 3 hours while being ultrasonicated. This treatment resulted in the formation of cocrystalline pigment, characterized by the X-ray diffractogram depicted in FIG. 3, which has intensity peaks at 7.4°, 10.2°, 12.7°, 13.2°, 16.0°, 17.3°, 18.5°, 22.4°, 24.4°, 25.5°, and 28.7° with respect to X-rays characteristic of Cu Kα at a wavelength of 1.541 Å of the Bragg angle 2θ.

Figure 2:
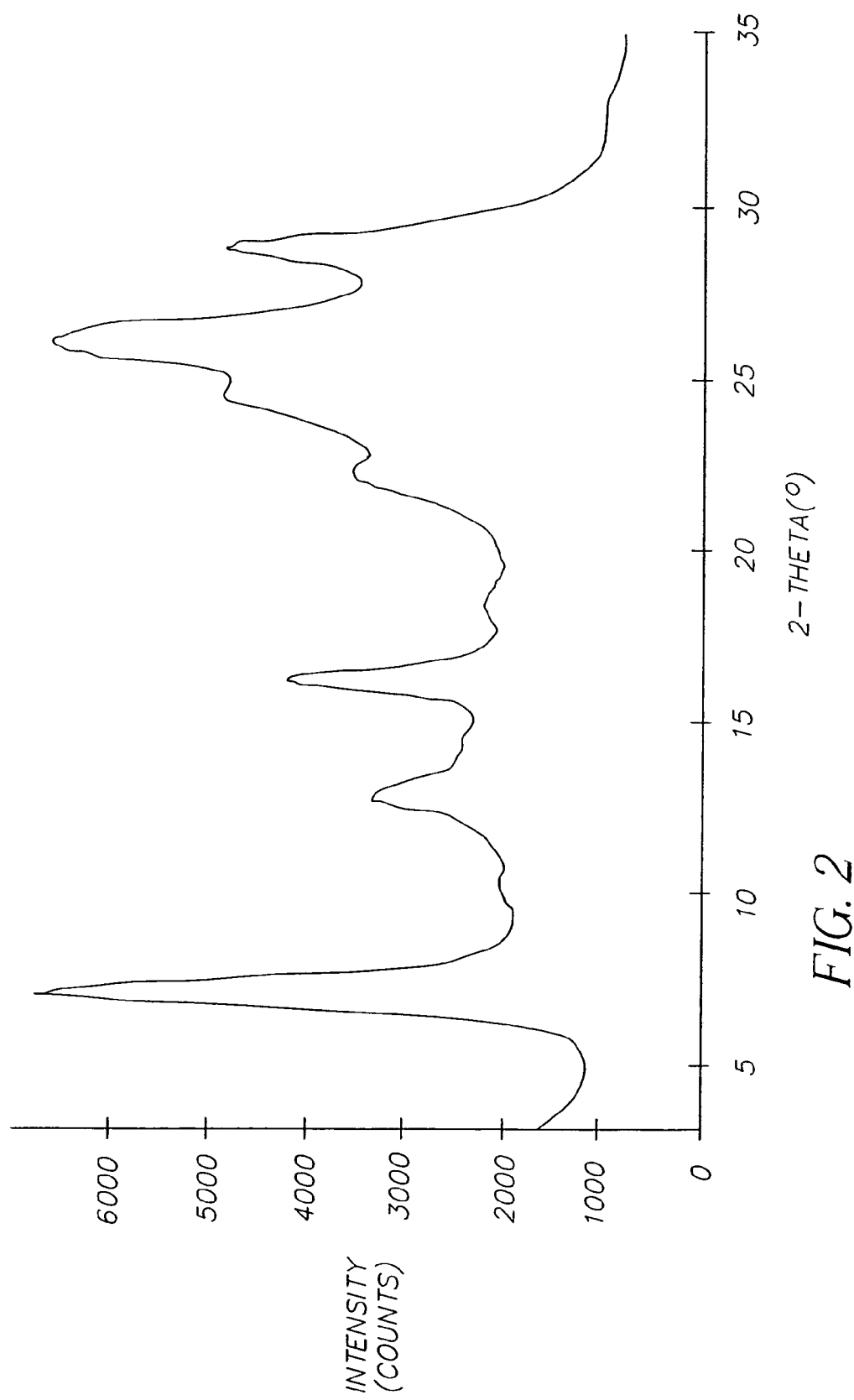
Figure 3:
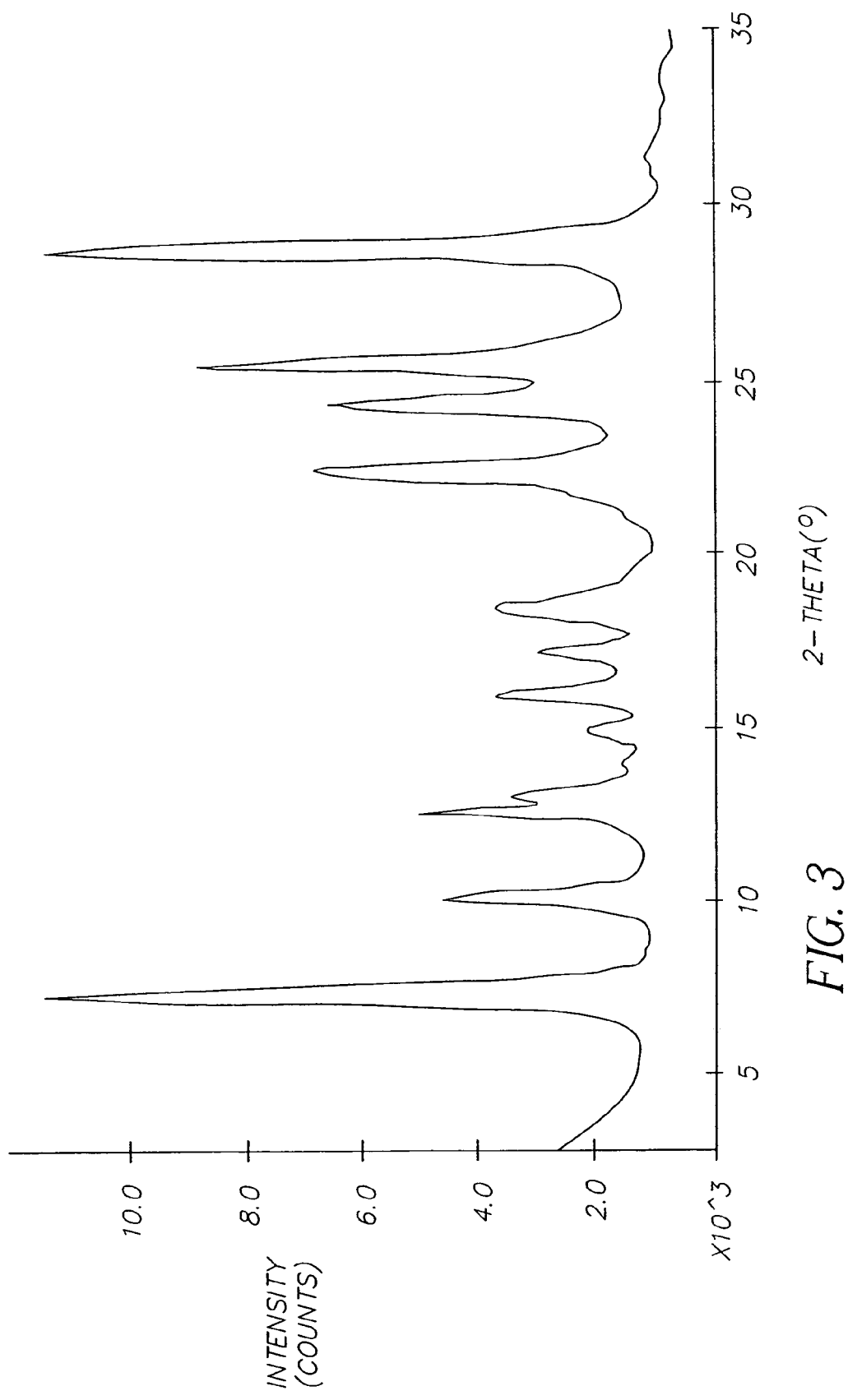
Figure 4:
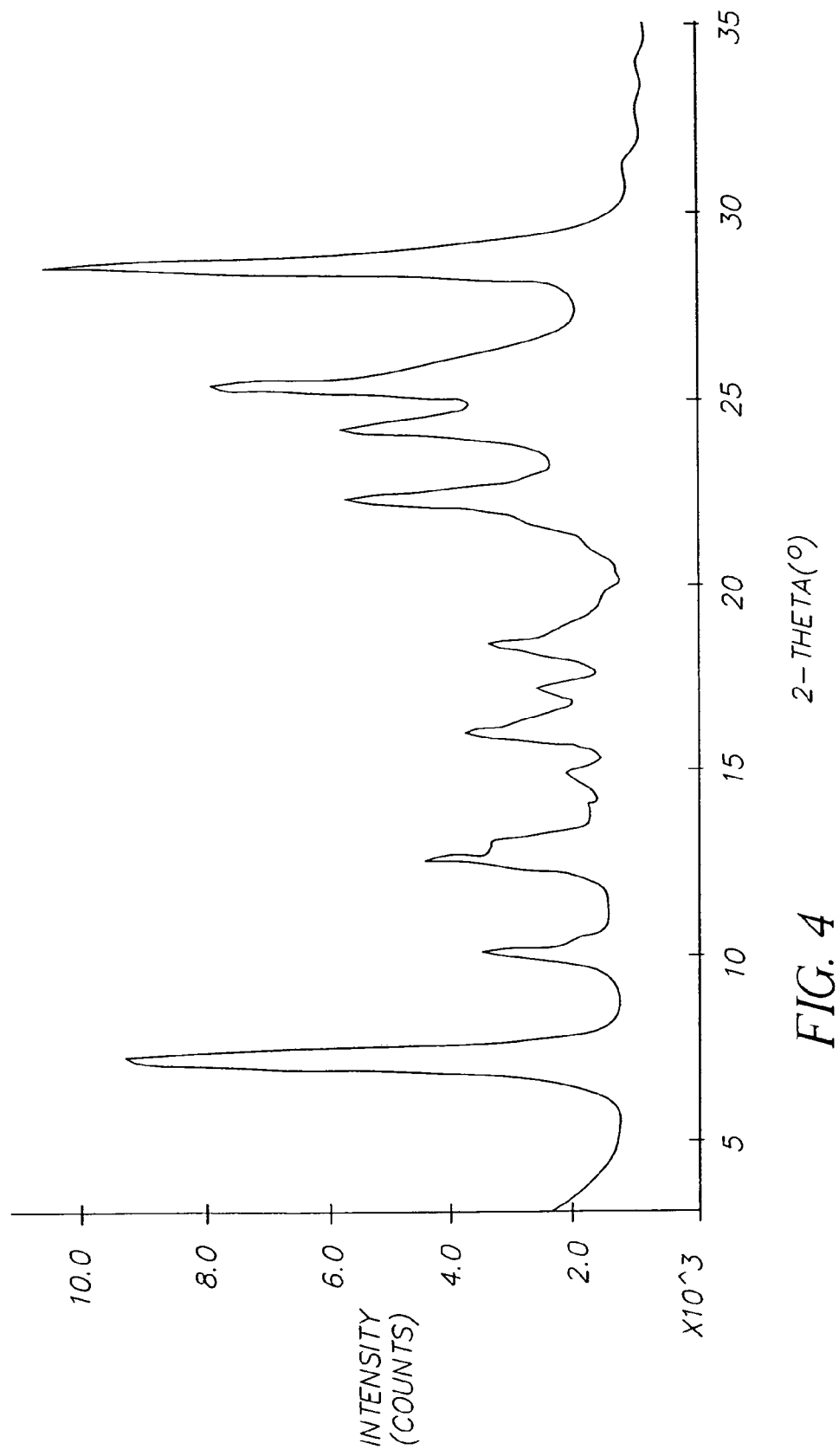
Figure 5:
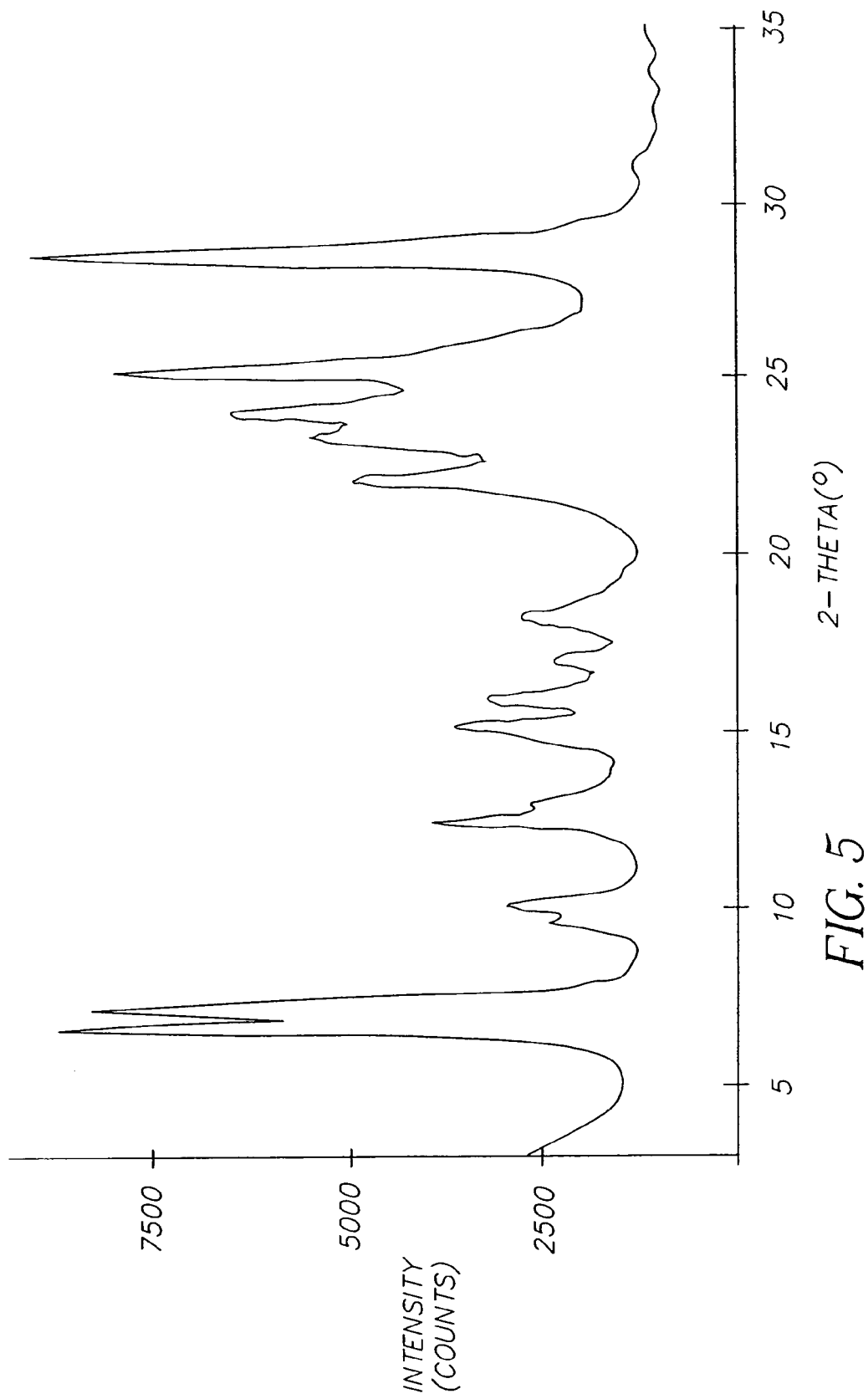
Figure 6:
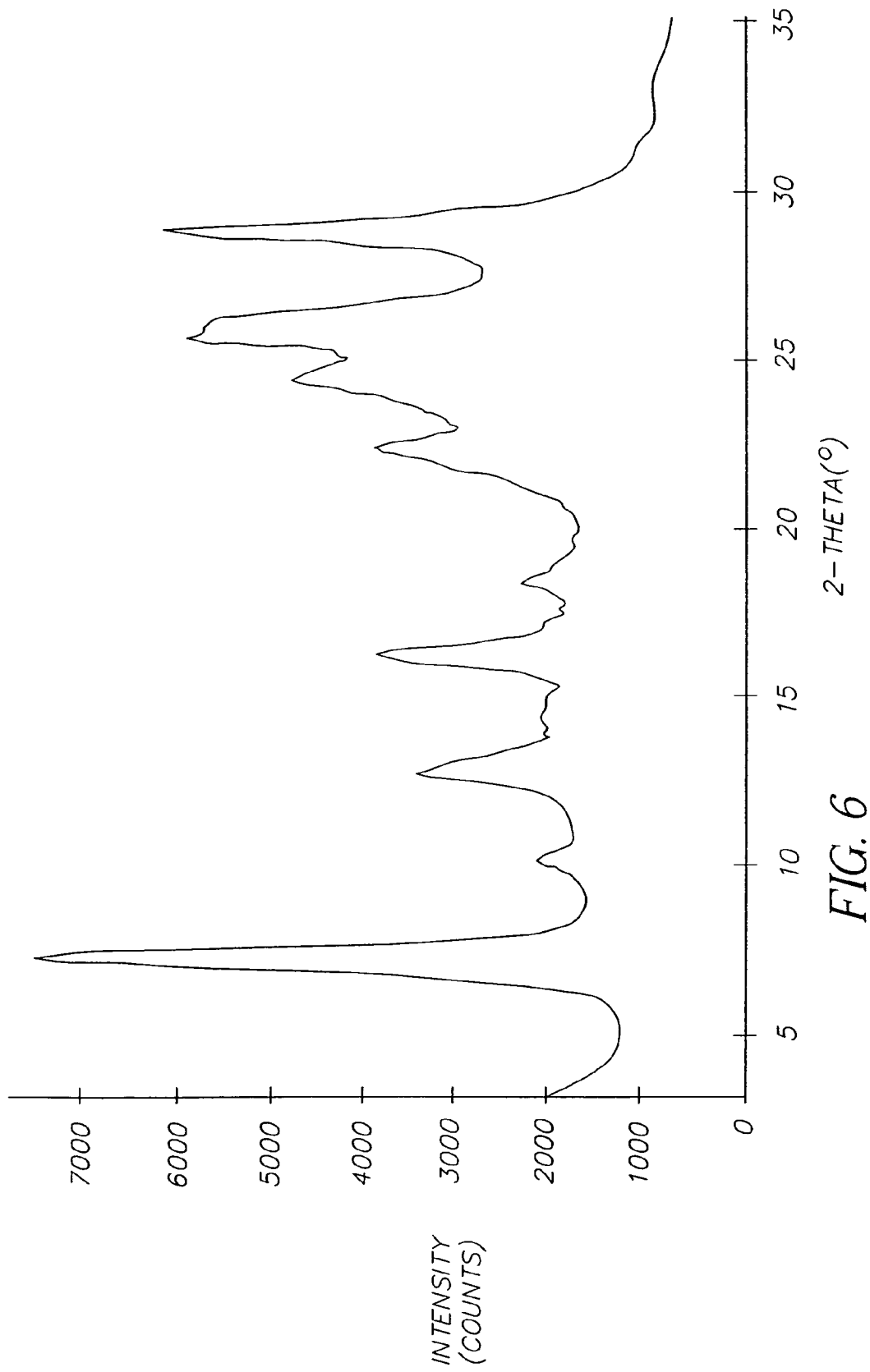

Comparison of FIG. 3 with FIG. 2 shows that the cocrystalline pigment obtained by ultrasonication in dichloromethane of the amorphized mixture of Example 1 is distinctly different from that produced by heat treatment of the amorphous pigment.

b) A sample of the heat-induced cocrystalline material of Example 2 was treated in dichloromethane for 3 hours while being ultrasonicated. The X-ray diffractogram of the resulting material, shown in FIG. 4, was substantially the same as that depicted in FIG. 3, indicating that ultrasonication in dichloromethane of the heated-induced cocrystalline material converted it to the same cocrystalline pigment as had been obtained by ultrasonic treatment of the amorphous pigment.

c) A sample of the amorphized mixture of Example 1 was treated with methanol for 3 hours while being ultrasonicated. The complex X-ray diffractogram of the resulting product, shown in FIG. 5, is indicative of the presence of two crystalline structures, one being attributed to TiOPc, the other to TiOFPc.

d) A sample of the heat-induced cocrystalline pigment of Example 2 was treated for 3 hours with methanol while being ultrasonicated. The X-ray diffractogram of the material so treated, shown in FIG. 6, was unexpectedly essentially unchanged from that depicted in FIG. 2 for the starting heat-induced cocrystalline pigment. This result is in marked contrast to that produced by ultrasonic treatment in dichloromethane of the heat-induced cocrystalline pigment, as described in b) above.

The foregoing result demonstrates that the cocrystalline pigment obtained by heat treatment of the amorphized TiOPc/TiOFPc mixture is a novel crystalline form, different from the previously known TiOPc/TiOFPc cocrystalline pigment produced by ultrasonic treatment of amorphized TiOPc/TiOFPc.

The invention has been described above with particular reference to preferred embodiments thereof, but it will be understood that variations and modifications can be effected within the spirit and scope of the invention, which is defined by the claims that follow.

What is claimed is:

1. A process for forming a cocrystalline mixture of titanyl phthalocyanine (TiOPc) and titanyl fluorophthalocyanine (TiOFPc) comprising:

dry milling a mixture of crude TiOPc and crude TiOFPc, thereby forming a dry amorphous pigment mixture of TiOPc and TiOFPc; and heating the dry amorphous pigment mixture at a temperature effective to form a cocrystalline composition comprising titanyl phthalocyanine (TiOPc) and titanyl fluorophthalocyanine (TiOFPc), said cocrystalline composition being characterized by an X-ray diffraction spectrum exhibiting intensity peaks at 7.2°, 12.9°, 16.3°, 22.3°, 24.6°, 26.2°, and 28.8° with respect to X-rays of Cu Kα at a wavelength of 1.54 1 Å of the Bragg angle 2θ.

2. The process of claim 1 wherein said dry amorphous pigment mixture is heated at a temperature of from about 150° C. to about 250° C.

3. The process of claim 2 wherein said dry amorphous pigment mixture is heated at a temperature of from about 170° C. to about 220° C.

4. The process of claim 1 wherein said dry amorphous pigment mixture is heated for from about 15 minutes to about 3 hours.

5. The process of claim 4 wherein said dry amorphous pigment mixture is heated for from about 30 minutes to about 2 hours.

6. The process of claim 1 wherein said cocrystalline composition contains TiOPc and TiOFPc in a TiOPc:TiOFPc weight ratio of from about 90:10 to about 50:50.

7. The process of claim 6 wherein said cocrystalline composition contains TiOPc and TiOFPc in a TiOPc:TiOFPc weight ratio of from about 75:25 to about 65:35.

\* \* \* \* \*